US00PP14606P29

(12) United States Plant Patent
Pierce

(10) Patent No.: US PP14,606 P2
(45) Date of Patent: Mar. 16, 2004

(54) CALIBRACHOA PLANT NAMED 'CAL ROSE'

(50) Latin Name: *Calibrachoa spp.*
Varietal Denomination: Cal Rose

(75) Inventor: Robert Osteen Pierce, Watsonville, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 37 days.

(21) Appl. No.: 10/389,045

(22) Filed: Mar. 13, 2003

(51) Int. Cl.[7] ..... A01H 5/00
(52) U.S. Cl. ..... Plt./263
(58) Field of Search ..... Plt./263

*Primary Examiner*—Anne Marie Grunberg
*Assistant Examiner*—Annette Para
(74) *Attorney, Agent, or Firm*—Jondle & Associates, PC

(57) ABSTRACT

'Cal Rose' is a new variety of Calibrachoa plant. This new variety has white colored flowers.

1 Drawing Sheet

Genus and species: Calibrachoa spp.
Variety denomination: 'Cal Rose'.

BACKGROUND OF THE INVENTION

'Cal Rose' originated from a hybridization made in the year 2000 in Gilroy, Calif. The female parent was a Calibrachoa breeding line known as 77-3, an ivory white proprietary line that is unnamed and unpatented. The male parent was Calibrachoa variety 166-1, a rose with a yellow throat proprietary line that is unnamed and unpatented.

'Cal Rose' is a product of a planned breeding program intended to create new calibrachoa plants with rose-colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield Mich. and Andijk, The Netherlands. The present invention has been found to retain its distinctive characteristics through successive propagations; and this novelty is firmly fixed.

Description of the genus Calibrachoa Llave & Lex

The genus Petunia was originally established in 1803 by A. L. Jussieu, who described both *P. parviflora* and *P. nyctaginifloa* as type species. Using a non-horticultural system that selected the first mentioned species as the type species (lectotype), N. L. Britton and H. A. Brown declared *P. parviflora* as the type species for Petunia in 1913.

During the 1980's and 1990, H. J. Wijsman published a series of articles regarding the ancestry of P. hybrida, the Garden Petunia, and the inter-relationship of several species classified as Petunia. These studies discovered that *P. hybrida* and its ancestrial species, *P. nyctaginiflora* (=*P. axillaris*) and *P. violacea* (=*P. integrifolia*), possessed 14 pairs of chromosomes while several other species, including *P. parviflora*, possessed 18 pairs of chromosomes. Since *P. parviflora* was the lectotype species for the Petunia genus, Wijsman and J. H. de Jong proposed transferring the 14 chromosome species to the genus Stimoryne. Horticulturists opposed reclassifying the Garden Petunia and in 1986, Wijsman proposed the alternative of making *P. nyctaginiflora* the lectotype species for Petunia and transferring the 18 chromosome. species to another genus. The I. N. G. Committee adopted this proposal. By 1990 Wijsman had transferred several species, including *P. parviflora* (=*C. parviflora*) to Calibrachoa, originally established by Llave and Lexarza in 1825. *Calibrachoa parviflora* (=*C. mexicana* Llave & Lexarza) is now the type species for the genus Calibrachoa.

Classification of the current Petunia and Calibrachoa species is still in progress. New species are also being identified. Consequently a proper description has not been written for the Calibrachoa genus. Calibrachoa can, however, be distinguished from Petunia based on the higher chromosome number, chromosome morphology, plant branching habit and type of flower bud aestivation. Whereas Petunia species bear a flower peduncle and one new stem from a node, Calibrachoa bear a flower peduncle and three stems. Petunia species have a cochlear corolla bud, a single outermost petal covers the other four, radially folded and terminally contorted petals. Calibrachoa flower buds are flat with all five petals linearly folded and the two lower petals forming a cover around the three other petals and fused together.

BRIEF DESCRIPTION OF THE PHOTOGRAPH

The accompanying colored photograph, illustrates the overall appearance of the cultivar Cal Rose, showing the colors as true as it is reasonably possible to obtain in colored reproduction of this type.

DETAILED DESCRIPTION OF THE NEW PLANT

The following traits and characteristics describe the new variety. The plant history was taken on 9 month old plants that were cut back numerous times prior to data readings being taken.

Classification:
*Family.*—Solanaceae.
*Species.*—Calibrachoa spp.
Growth:
*Form.*—Semi upright and decumbent.
*Habit.*—Good vigorous habit, well branched, full plant.

*Height.*—15–20 cm.
*Width.*—45–55 cm.
*Time to produce a finished flowering plant.*—9–11 weeks.
*Outdoors plant performance.*—Full sun, free flowering though the summer, some heat tolerance, used as a hanging plant; in mixed container plantings; mass planting in a bed.
*Time to initiate and develop roots.*—18–23 days.
*Root description.*—White, fibrous.

Stems:
*Stem color.*—R.H.S. 144B (yellow-green).
*Stem length.*—30–40 cm.
*Stem diameter.*—0.15–0.2 cm.
*Stem internodes length.*—0.6–1.5 cm.
*Stem texture.*—Many glandular hairs of various sizes, some with a rose colored hue.
*Stem anthocyanin.*—Yes, in irregular patches on upper-side.
*Pedicel color.*—RHS 144B (yellow-green).
*Pedicel length.*—1.5–1.7 cm.
*Pedicel diameter.*—0.1 cm.
*Pedicel texture.*—Many glandular hairs of various sizes.

Leaves:
*Arrangement.*—Alternate; upper leaves sub-opposite.
*Leaf color.*–Upper side, RHS 137A (green). Underside, RHS 137C (green).
*Leaf length.*—2.3–2.6 cm.
*Leaf width.*—0.6–1.0 cm.
*Leaf blade shape.*—Oblong/Elliptic.
*Leaf margin.*—Entire.
*Leaf apex aspect.*—Obtuse.
*Leaf base aspect.*—Acuminate.
*Leaf texture.*—Many glandular hairs of various sizes.
*Venation.*—Pinnate.
*Venation color.*—RHS 144A (yellow-green).
*Petiole color.*—RHS 144A (yellow-green).
*Petiole length.*—0.3–0.5 cm.
*Petiole width.*—0.15 cm.
*Petiole texture.*—Many glandular hairs of various sizes.

Bud:
*Color at tight bud.*—RHS 77A (purple) base color; RHS N77A (purple) veining but lighter.
*Bud shape.*—Oblong.
*Bud diameter.*—0.4 cm.
*Bud length.*—1.3–1.9 cm.

Flowers:
*Blooming habit.*—Continuous throughout the growing season. Good floriferousness.
*Inflorescence type.*—Flowers solitary in upper leaf axis.
*Floret type.*—Funnel form, 5 lobed petals, fused at base.
*Young flower color.*—Bright RHS N74A (purple) base color with more red tones; N77A (purple) mid-veins; RHS N77A (purple) and RHS 59A (red-purple) throat blush.
*Young flower floret diameter.*—2.4–2.7 cm.
*Mature flower color.*—Front side, Bright RHS N74A (red-purple) base color, with more red tones, but less red tones at the lobation point; RHW#N77A mid veins; RHS N77A (purple) and RHS 59A (red-purple) blush at the flare.
*Mature flower color.*—Underside, RHS 77B (purple) base color; RHS N77A&B (purple) secondary veins.
*Corolla tube color inside.*—RHS 6A (yellow) base color; RHS 183B (greyed-purple) veining on upper portion.
*Corolla tube length.*—1.2–1.4 cm.
*Corolla outside texture.*—Many glandular hairs various sizes.
*Flower (limb) diameter.*—2.6–3.0 cm.
*Petal apex shape.*—Retuse.
*Petal base shape.*—Fused.
*Petal margin.*—Entire.
*Waviness of petals.*—Weak to none.
*Petal lobation.*—Moderate.
*Petal texture.*—Papillose.
*Sepals.*—5, fused at base.
*Sepal color.*—RHS 143A (green) but a little greener.
*Sepal length.*—1.1–1.4 cm.
*Sepal width.*—0.2–0.25 cm.
*Sepal shape*—Oblong.
*Sepal apex.*—Acute/Obtuse.
*Sepal texture.*—Many glandular hairs various sizes.
*Lastingness of individual blooms.*—5–8 days.
*Fragrance.*—None.

Reproductive organs:
*Stamens.*—5; 2 taller, 3 shorter.
*Filament color.*—RHS 142D (green).
*Pollen color.*—RHS 7A (yellow).
*Pistil.*—One.
*Stigma color.*—RHS 143C (green).
*Style color.*—RHS 142C (green).
*Fruit seed set.*—Not observed.

Disease and Insect Resistance

Not observed.

COMPARISON WITH MOST SIMILAR VARIETY

'Cal Rose' differs from the female parent 77-3 in the following ways: 'Cal Rose' has rose-colored flowers while 77-3 has ivory white flowers. 'Cal Rose' has smaller leaves and more prostrate than 77-3.

'Cal Rose' differs from the male parent 166-1 in the following ways: 'Cal Rose' has more centered flowers, earlier flowering and more basal branching than 166-1.

What is claimed is:

1. A new and distinct Calibrachoa plant as shown and described herein.

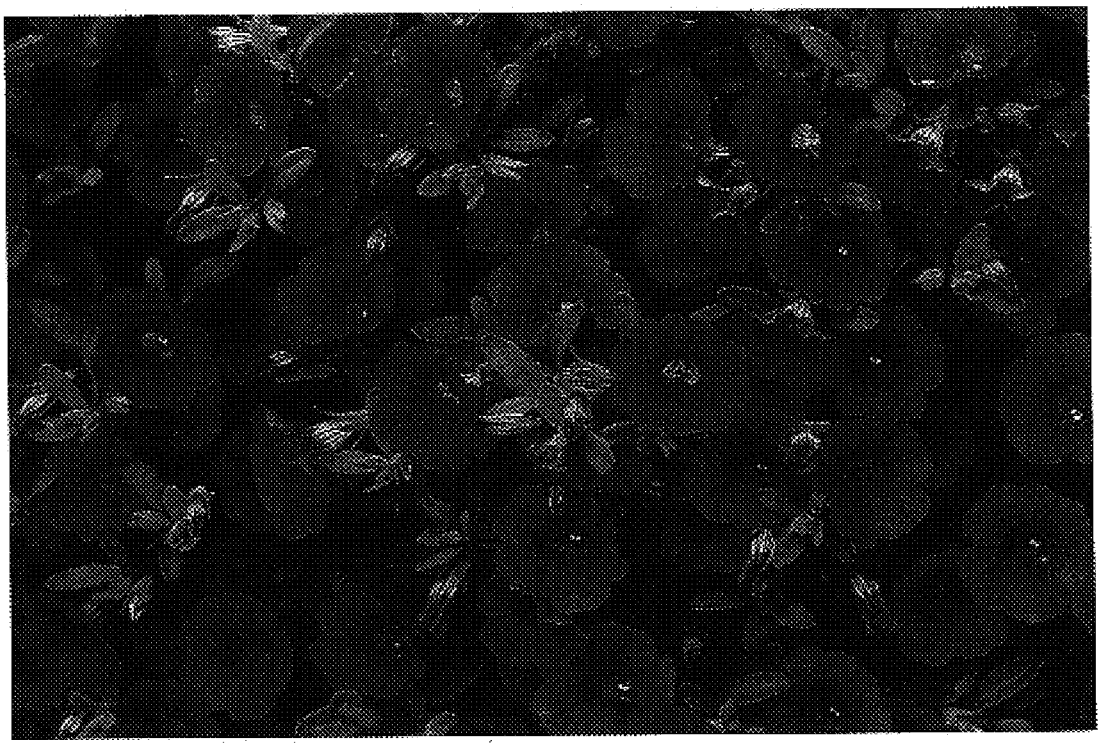

* * * * *